United States Patent [19]

Boothroyd et al.

[11] Patent Number: 5,250,289
[45] Date of Patent: Oct. 5, 1993

[54] SUNSCREEN COMPOSITIONS

[75] Inventors: Stephen Boothroyd, Nottingham; Edward Galley, Newark; Arija M. Stammers, Nottingham, all of England

[73] Assignee: The Boots Company PLC, Nottingham, England

[21] Appl. No.: 464,609

[22] Filed: Jan. 11, 1990

Related U.S. Application Data

[63] Continuation of Ser. No. 222,900, Jul. 22, 1988, abandoned.

[30] Foreign Application Priority Data

Jul. 24, 1987 [GB] United Kingdom ............... 8717662

[51] Int. Cl.$^5$ .................... A61K 7/42; A61K 7/44; A61K 7/48; A61K 9/10
[52] U.S. Cl. ................................. 424/59; 424/60; 514/938; 514/939
[58] Field of Search ........................... 424/59, 60

[56] References Cited

U.S. PATENT DOCUMENTS

| | | | |
|---|---|---|---|
| 2,175,213 | 10/1939 | Parsons | 424/59 |
| 2,826,169 | 3/1958 | LeVeen | 424/59 |
| 3,146,170 | 8/1964 | Battista | 424/65 |
| 3,697,642 | 10/1972 | Madigan | 424/59 |
| 4,683,134 | 7/1987 | Palinczar | 424/59 |
| 4,698,178 | 10/1987 | Huttinger et al. | 424/59 |
| 4,710,373 | 12/1987 | Nakamura et al. | 424/59 |
| 4,731,242 | 3/1988 | Palinczar | 424/59 |

FOREIGN PATENT DOCUMENTS

| | | | |
|---|---|---|---|
| 0125779 | 11/1984 | European Pat. Off. | 424/59 |
| 47-42502 | 10/1972 | Japan | 424/59 |
| 1140870 | 1/1969 | United Kingdom | 574/772 |
| 1387281 | 3/1975 | United Kingdom | 424/59 |
| 1604350 | 12/1981 | United Kingdom | 424/59 |
| 2155337 | 3/1984 | United Kingdom | 424/59 |
| 2184356 | 6/1987 | United Kingdom | 424/59 |

OTHER PUBLICATIONS

Bennett, Aug. 1941, Cosmetic Formulary.
Derwent Abstract of Japanese Pat. No. 9000450-A, May 1, 1974.
49912 K/21 D21 E32 Shiseido KK, Abstract.
85-232456/38 D21 A96 E12 (E37) Kane 13 Jan. 1984, Abstract.
Chemical Abstracts 107 161409h of Japanese Pat. Appln. 62/145011 published 29 Jun. 1987.
The paragraph entitled "Unique Screen Agent" published as part of an article entitled Sunshine '82 in the Jan. 1982 edition of Manufacturing Chemist.

*Primary Examiner*—Dale R. Ore
*Attorney, Agent, or Firm*—Ostrolenk, Faber, Gerb & Soffen

[57] ABSTRACT

A sunscreening composition which comprises a water-in-oil emulsion which comprises a) 0.5 to 30% by weight of titanium dioxide having a mean primary particle size of less than 100 nm, b) 5 to 20% by weight of an oil phase, c) 1 to 15% by weight of an emulsifier, and d) at least 40% by weight of an aqueous phase. The titanium dioxide may be coated with aluminium stearate. Further sunscreening agents may be included. The oil phase may be a hydrocarbon oil, a wax, a natural oil, a silicone oil or a mixture. Preferred emulsifiers are sesquioleates such as polyglyceryl-2-sesquioleate or sorbitan sesquioleate, polyethoxylated esters of derivatives of natural oils such as polyethoxylated esters of hydrogenated castor oil or silicone emulsifiers such as silicone polyols.

7 Claims, No Drawings

SUNSCREEN COMPOSITIONS

This application is a continuation of application Ser. No. 07/222,900 filed Jul. 22, 1988, now abandoned.

The present invention relates to sunscreen compositions. The term "sunscreen" is used herein to encompass tanning lotions, sunscreens and sunblockers which are intended for use on the body to provide protection against the sun's rays or other UV sources.

Heretofore sunscreen compositions have been prepared either as oil-in-water or water-in-oil emulsions containing organic sunscreen agents which could be formulated equally successfully in either of the above emulsion systems. More recently sunscreen compositions have been proposed which contain as the sunscreening agent, titanium dioxide. Titanium dioxide sunscreen formulations have heretofore been prepared as oil-in-water emulsions. The present invention stems from the applicants' discovery that titanium dioxide is more effective as a sunscreen when it is formulated as a water-in-oil emulsion.

The present invention provides a sunscreen composition which comprises a water-in-oil emulsion which comprises a) 0.5 to 30% by weight of titanium dioxide having a mean primary particle size of less than 100 nm, b) 5 to 20% by weight of an oil phase, c) 1 to 15% by weight of an emulsifier, and d) at least 40% by weight of an aqueous phase.

The titanium dioxide in the sunscreen compositions preferably has a mean primary particle size of between 1 and 100 nm preferably between 5 and 50 nm most preferably around 30 nm. Titanium dioxide of the above mean primary particle size is usually referred to as "microfine". It is possible for the primary particles in microfine titanium dioxide to agglomerate in the compositions of the present invention but the sunscreening activity remains that of the individual primary particles that make up the agglomerate. The titanium dioxide may have an anatase, rutile or amorphous structure. The particles are preferably uncoated but may be provided with a coating of an aluminium compound such as aluminium stearate to minimise light-induced reduction of the titanium dioxide and to aid dispersion of the particles in the water-in-oil emulsions of the present invention. Microfine titanium dioxide is available from Degussa under the trade designation P25 and from Teikoku Kako Co. Ltd. under the trade designation MT150W. Titanium dioxide coated with aluminium stearate is available from Teikoku Kako Co. Ltd. under the trade designation MT100T. This last mentioned material is hydrophobic whereas the uncoated materials are not. The amount of titanium dioxide present in any particular composition according to the present invention depends on the use for which the composition is intended. Amounts as low as 1% may be sufficient in the so-called suntanning products which are not intended to prevent the sun's rays reaching the skin whereas the so-called sunblocks which are intended to prevent substantially all of the sun's rays reaching the skin may require levels of 15 to 20%. Sunscreen compositions will more usually contain 2.5 to 10% of titanium dioxide.

Other sunscreening agents may be incorporated into the compositions of the present invention. Examples of suitable further sunscreening agents include a) p-aminobenzoic acids, its esters and derivatives (for example, 2-ethylhexyl p-dimethylaminobenzoate), b) methoxycinnamate esters (for example, 2-ethylhexyl p-methoxycinnamate, 2-ethoxyethyl p-methoxycinnamate or α, β-di-(p-methoxycinnamoyl)-α'-(2-ethylhexanoyl)-glycerin), c) benzophenones (for example oxybenzone), d) dibenzoylmethanes and e) salicylate esters. Any additional sunscreening agent is present in an amount from 0.1 to 10% by weight of the composition.

The oil phase of the water-in-oil emulsions of the present invention may comprise a) hydrocarbon oils such as paraffin or mineral oils, b) waxes such as beeswax or paraffin wax, c) natural oils such as sunflower oil, apricot kernel oil, shea butter or jojoba oil, d) silicone oils such as dimethicone, cyclomethicone or cetyldimethicone or e) mixtures thereof. In preferred compositions of the present invention the oil phase comprises 10–50, more preferably 20 to 40% of the composition. It has been found that compositions in which the oil phase comprises silicone oils or a mixture of silicone oils and hydrocarbon oils and waxes are particularly effective in the sunscreening test described in detail hereinafter.

The emulsifiers used may be any emulsifiers known in the art for use in water-in-oil emulsions. It has been found that particularly effective sunscreen compositions can be prepared by using an emulsifier or mixture of emulsifiers selected from a) sesquioleates such as polyglyceryl-2-sesquioleate (available commercially for example under the trade name Hostacerin WO) or sorbitan sesquioleate (available commercially for example under the trade name Arlacel 83), b) ethoxylated esters of derivatives of natural oils such as the polyethoxylated ester of hydrogenated castor oil (available commercially for example under the trade name Arlacel 989), c) silicone emulsifiers such as silicone polyols (available commercially for example under the trade name ABIL WS08) or d) mixtures thereof. The amount of emulsifier present in the compositions of the present invention is preferably in the range 2–10%. In preferred compositions of the present invention the emulsifier is a mixture of polyglyceryl-2-sesquioleate and polyethoxylated esters of hydrogenated castor oil. In particularly preferred compositions of the present invention the emulsifier is a silicone polyol which forms around 2 to 4% of the composition.

The compositions of the present invention may additionally comprise other components which will be well known to those skilled in the art for example emolients such as isopropyl myristate or a triglyceride of a fatty acid (e.g. lauric triglyceride or capric/caprylic triglyceride), humectants such as glycerin or 1,3-butyleneglycol, antioxidants such a DL-A-tocopherylacetate or butylated hydroxytoluene, emulsion stabilising salts such as sodium chloride, film formers to assist spreading on the surface of the skin such as alkylated polyvinylpyrrolidone, preservatives such as bronopol isothiazolone or diazolidinylurea, perfumes and colouring.

The efficacy of the compositions may be measured in user tests, i.e. in vivo, or, more conveniently, in a model system disclosed by Dr. M. Stockdale at the Joint Symposium of the Society of Cosmetic Scientists and the Societe Francaise de Cosmetologie, held in Stratford, UK in April 1986 and subsequently published in the International Journal of Society of Cosmetic Scientists 9 pp 85–98 (1987). Essentially, a cast of human skin is taken so that the topography of the skin is reproduced exactly. The first (negative) cast is made from silicone rubber and then a second (positive) cast is made from an ultraviolet (UV) transparent material such as Luviset CAP-X (BASF) in ethanol. Luviset CAP-X is a hair lacquer. UV light from 900W Xenon Arc Clinical Photo-Irradiator (Applied Photophysics Ltd.) is supplied via a 1 m×5 mm flexible light guide (Applied Photophysics Ltd.) and passed through the second cast to give a 2cm diameter beam on a thermopile or a UV-310 sensor coupled to a UVX Radiometer (Ultra Violet Products Inc.; USA). The product to be tested was dispensed onto the second cast and evenly spread on the surface of the cast. A protection index can then be derived by dividing (Detector reading without the product) by (Detector reading with the product).

The invention is illustrated by the following Examples 1 to 10 which are formulated as water-in-oil emulsions. Examples 1 to 10 are given by way of example only. Comparative Examples A to E form no part of the present invention and are formulated as oil-in-water emulsions. The results of tests performed as described above to determine the protection index are given below and it can be seen that the Examples illustrating compositions of the present invention show a much higher protection index than is obtained with the Comparative Examples.

| Example | Protection Index | % Improvement |
|---------|------------------|---------------|
| 1 | 11 | 120% |
| A | 5 | |
| 2 | 6 | 100% |
| B | 3 | |
| 7 | 6 | 50% |
| C | 4 | |
| 8 | 10 | 100% |
| D | 5 | |
| 6 | 14 | 75% |
| E | 8 | |
| 10 | 16 | 78% |
| F | 9 | |

EXAMPLE 1

| | |
|---|---|
| 1) A mixture of polyglyceryl-2-sesquioleate, beeswax, mineral oil, magnesium stearate and aluminium stearate (sold under the trade name Hostacerin WO) | 6% |
| 2) Polyoxyethylene ester of hydrogenated castor oil (sold under the trade name Arlacel 989) | 3% |
| 3) White Soft Paraffin | 5% |
| 4) Liquid Paraffin | 8% |
| 5) Alkylated polyvinylpyrrolidone (sold under the trade name Unimer U151) | 2% |
| 6) Isopropyl myristate | 14% |
| 7) Titanium dioxide (sold under the trade designation P25) | 10% |
| 8) Purified water | to 100% |

Components 1 to 6 were mixed together and heated to 70° C. and the titanium dioxide (component 7) dispersed in the mixture using a high shear mixer/homogeniser (Silverson). The water heated to 70° C. was added slowly with stirring. The resulting mixture was homogenised using a high shear/mixer homogeniser to give a cream.

EXAMPLE 2

| | |
|---|---|
| 1) A mixture of polyglyceryl-2-sesquioleate, beeswax, mineral oil, magnesium stearate and aluminium stearate (sold under the trade name Hostacerin WO) | 6% |
| 2) Polyoxyethylene ester of hydrogenated castor oil (sold under the trade name Arlacel 989) | 3% |
| 3) White Soft Paraffin | 5% |
| 4) Liquid Paraffin | 6% |
| 5) Alkylated polyvinylpyrrolidone (sold under the trade name Unimer U151) | 2% |
| 6) Isopropyl myristate | 9% |
| 7) Titanium dioxide (sold under the trade designation P25) | 5% |
| 8) Purified water | to 100% |

The above components were formulated as described in Example 1 to give a cream.

EXAMPLE 3

| | |
|---|---|
| 1) A mixture of polyglyceryl-2-sesquioleate, beeswax, mineral oil, magnesium stearate and aluminium stearate (sold under the trade name Hostacerin WO) | 6% |
| 2) Polyoxyethylene ester of hydrogenated castor oil (sold under the trade name Arlacel 989) | 3% |
| 3) White Soft Paraffin | 5% |
| 4) Liquid Paraffin | 8% |
| 5) Alkylated polyvinylpyrrolidone (sold under the trade name Unimer U151) | 2% |
| 6) Isopropyl myristate | 14% |
| 7) Titanium dioxide (sold under the trade designation MT100T) | 10% |
| 8) Purified water | to 100% |

The above components were formulated as described in Example 1 to give a cream.

EXAMPLE 4

| | |
|---|---|
| 1) A mixture of polyglyceryl-Z-sesquioleate, beeswax, mineral oil, magnesium stearate and aluminium stearate (sold under the trade name Hostacerin WO) | 6% |
| 2) Polyoxyethylene ester of hydrogenated castor oil (sold under the trade name Arlacel 989) | 3% |
| 3) White Soft Paraffin | 5% |
| 4) Liquid Paraffin | 8% |
| 5) Alkylated polyvinylpyrrolidone (sold under the trade name Unimer U151) | 2% |
| 6) Isopropyl myristate | 10% |
| 7) 2-ethylhexyl p-dimethylaminobenzoate (sold under the trade name Escalol 507) | 4% |
| 8) Titanium dioxide (sold under the trade designation MT100T) | 5% |
| 9) Purified water | to 100% |

Components 1 to 7 were mixed together and heated to 70° C. and the titanium dioxide (component 8) dispersed in the mixture using a high shear mixer/homogeniser (Silverson). The water heated to 70° C. was added slowly with stirring. The resulting mixture was homogenised using a high shear/mixer homogeniser to give a cream.

EXAMPLE 5

| | |
|---|---|
| 1) A mixture of polyglyceryl-2-sequiolate, beeswax, mineral oil, magnesium stearate and aluminium stearate (sold under the trade name Hostacerin WO) | 5.4% |
| 2) Polyoxyethylene ester of hydrogenated castor oil (sold under the trade name Arlacel 989) | 2.7% |

| | | |
|---|---|---|
| 3) Isopropyl myristate | 5% | |
| 4) Cetyl dimethicone (sold under the trade name ABIL 9801) | 8% | |
| 5) Dimethicone silicone fluid (30000 cps) | 1% | |
| 6) 2-ethylhexyl p-dimethylaminobenzoate (sold under the trade name Escalol 507) | 4% | |
| 7) Cyclomethicone (sold under the trade name Dow Corning 344) | 2% | |
| 8) Siliconised talc | 2% | |
| 9) A mixture of liquid paraffin and polyethylene (sold under the trade name Pionier PLW) | 10% | |
| 10) Titanium dioxide (sold under the trade designation MT 100T) | 8% | |
| 11) Purified water | to 100% | |

Components 1 to 9 were mixed together and heated to 70° C. and the titanium dioxide (component 10) dispersed in the mixture using a high shear mixer/homogeniser (Silverson). The water heated to 70° C. was added slowly with stirring. The resulting mixture was homogenised using a high shear/mixer homogeniser to give a cream.

EXAMPLE 6

| | |
|---|---|
| 1) Silicone polyol (sold under the trade name ABIL WS08) | 5% |
| 2) Isopropyl myristate | 9% |
| 3) Light liquid paraffin | 6% |
| 4) Sunflower oil | 3% |
| 5) Cyclomethicone (sold under the trade name Dow Corning 344) | 4% |
| 6) Glycerin | 2% |
| 7) Titanium dioxide (sold under the trade designation P25) | 10% |
| 8) Purified water | to 100% |

Components 6 and 8 were mixed together and added very slowly with stirring to Components 1 to 5 which had been previously mixed together. The titanium dioxide (Component 7) was then dispersed into the mixture using a high shear mixer/homogeniser (Silverson) to give a cream.

EXAMPLE 7

| | |
|---|---|
| 1) Isopropyl myristate | 9% |
| 2) Light liquid paraffin | 6% |
| 3) White soft paraffin | 3% |
| 4) Silicone polyol (sold under the trade name ABIL WS08) | 5% |
| 5) Cyclomethicone (sold under the trade name Dow Corning 344) | 4% |
| 6) Sodium chloride | 2% |
| 7) Glycerin | 5% |
| 8) Titanium Dioxide (sold under the trade designation MT150W) | 5% |
| 9) Purified water | to 100% |

Components 1 to 5 were mixed together and the titanium dioxide dispersed in the mixture using a high shear mixer/homogeniser (Silverson). The water, sodium chloride and glycerin were mixed and added slowly with stirring. The resulting mixture was homogenised to give a light cream/lotion.

EXAMPLE 8

| | |
|---|---|
| 1) Isopropyl myristate | 9% |
| 2) White soft paraffin | 3% |
| 3) Silicone polyol (sold under the trade name ABIL WS08) | 5% |
| 4) Cyclomethicone (sold under the trade name Dow Corning 344) | 4% |
| 5) Sodium chloride | 2% |
| 6) Glycerin | 5% |
| 7) Titanium Dioxide (sold under the trade designation MT150W) | 10% |
| 8) Purified water | to 100% |

The above components were formulated as in Example 7 to give a light cream/lotion.

EXAMPLE 9

| | |
|---|---|
| 1) Isopropyl myristate | 9% |
| 2) Light liquid paraffin | 6% |
| 3) White soft paraffin | 3% |
| 4) Silicone polyol (sold under the trade name ABIL WS08) | 5% |
| 5) Cyclomethicone (sold under the trade name Dow Corning 344) | 4% |
| 6) Sodium chloride | 2% |
| 7) Glycerin | 5% |
| 8) Titanium Dioxide (sold under the trade designation MT100T) | 10% |
| 9) Purified water | to 100% |

The above components were formulated as in Example 7 to give a light cream/lotion.

EXAMPLE 10

| | |
|---|---|
| 1) Microcrystalline wax (sold under the trade name Okerin 239) | 2% |
| 2) Silicone polyol (sold under the trade name ABIL WS08) | 5% |
| 3) White soft paraffin | 3% |
| 4) Light liquid paraffin | 3% |
| 5) Apricot Kernel Oil | 0.5% |
| 6) Cyclomethicone (sold under the trade name Dow Corning 345) | 6.5% |
| 7) Cetyl dimethicone (sold under the trade name ABIL 9801) | 1% |
| 8) Titanium Dioxide (sold under the trade designation MT100T) | 10% |
| 9) Glycerin | 5% |
| 10) Sodium chloride | 2% |
| 11) Isothiazolone E (sold under the trade name Kathon CG) | 0.05% |
| 12) Diazolidinyl urea (sold under the trade name Germall II) | 0.2% |
| 13) Purified water | to 100% |

The above components were formulated as described in Example 7 except that the preservatives (Components 11 and 12) were incorporated into the water phase and the resulting product was a heavy cream.

EXAMPLE 11

| | |
|---|---|
| 1) Sorbitan sesquioleate (sold under the trade name Arlacel 83) | 3 |
| 2) Trilaurin (a triglyceride of lauric acid sold under the trade name Softisan 100) | 1.5 |
| 3) White soft paraffin | 6 |
| 4) Shea Butter | 0.5 |
| 5) Jojoba oil | 0.5 |
| 6) Capric/caprylic triglyceride (sold under the trade name Miglyol 810) | 3 |
| 7) 2-Ethylhexyl p-methoxycinnamate (sold under the trade name Parsol MCX) | 1 |
| 8) DL-A-Tocopheryl Acetate | 0.5 |
| 9) Butylated hydroxytoluene | 0.08 |

| | |
|---|---|
| 10) A mixture of cyclomethicone and dimethicone copolyol (sold under the trade name Dow Corning 3225C) | 12 |
| 11) Cyclomethicone (sold under the trade name Dow Corning 345) | 8 |
| 12) Dimethicone (sold under the trade name F111/100) | 2 |
| 13) Titanium dioxide (sold under the trade designation MT100T) | 5 |
| 14) Sodium citrate | 1 |
| 15) Sodium pyrrolidone carboxylate (sold under the trade name Ajidew N50) | 1 |
| 16) Bronopol | 0.02 |
| 17) Glycerin | 2 |
| 18) 1,3-Butylene glycol | 1.5 |
| 19) Purified water | to 100 |

Components 1 to 12 were mixed and heated to 70° C. and the titanium dioxide dispersed in the mixture using a high shear mixer/homogeniser (Silverson). Components 14 to 19 were mixed and added slowly with stirring. The resulting mixture was homogenised to give a lotion.

COMPARATIVE EXAMPLE A

| | |
|---|---|
| 1) Ethoxylated (2) stearyl alcohol (sold under the trade name Brij 72) | 2 |
| 2) Ethoxylated (21) stearyl alcohol (sold under the trade name Brij 721) | 1 |
| 3) Cetyl alcohol | 3 |
| 4) Light liquid paraffin | 7 |
| 5) Dimethicone (30000 cps) | 5 |
| 6) 1,3-Butylene glycol | 3 |
| 7) Film-forming humectant (sold under the the trade name Lubrajel) | 2 |
| 8) Titanium Dioxide (sold under the trade designation P25) | 10 |
| 9) Purified water | to 100 |

Components 1 to 6 were mixed and heated to 70° C. and the titanium dioxide dispersed therein using a high shear/mixer homogeniser (Silverson). Components 7 and 9 were mixed, heated to 70° C. and added to the remaining ingredients with stirring. The resulting mixture was homogenised to give a cream.

COMPARATIVE EXAMPLE B

| | |
|---|---|
| 1) Cetostearyl alcohol | 3 |
| 2) Ethoxylated stearyl alcohol (sold under the trade name Cromul EM 1207) | 2 |
| 3) Ethoxylated (20) stearyl alcohol (sold under the trade name Volpo CS20) | 2 |
| 4) Liquid paraffin | 1 |
| 5) Hydroxyethylcellulose (sold under the trade name Natrosol 250HHR) | 0.2 |
| 6) Titanium dioxide (sold under the trade designation P25) | 5 |
| 7) Purified water | to 100 |

Components 1 to 4 were mixed and heated to 70° C. and the titanium dioxide dispersed therein using a high shear mixer/homogeniser (Silverson). Components 5 and 7 were mixed, heated to 70° C. and added to the remaining ingredients with stirring. The resulting mixture was homogenised to give a cream.

COMPARATIVE EXAMPLE C

| | |
|---|---|
| 1) Ethoxylated (2) stearyl alcohol (sold under the trade name Brij 72) | 2 |
| 2) Ethoxylated (21) stearyl alcohol (sold under the trade name Brij 721) | 1 |
| 3) Cetyl alcohol | 3 |
| 4) Light liquid paraffin | 7 |
| 5) 1,3-Butylene glycol | 3 |
| 6) Titanium dioxide (sold under the trade designation MT150W) | 5 |
| 7) Purified water | to 100 |

Components 1 to 4 were mixed and heated to 70° C. and the titanium dioxide dispersed therein using a high shear mixer/homogeniser (Silverson). Components 5 and 7 were mixed, heated to 70° C. and added to the remaining ingredients with stirring. The resulting mixture was homogenised to give a soft cream/lotion.

COMPARATIVE EXAMPLE D

| | |
|---|---|
| 1) Ethoxylated (2) stearyl alcohol (sold under the trade name Brij 72) | 2 |
| 2) Ethoxylated (21) stearyl alcohol (sold under the trade name Brij 721) | 1 |
| 3) Cetyl alcohol | 3 |
| 4) Light liquid paraffin | 7 |
| 5) 1,3-Butylene glycol | 3 |
| 6) Titanium dioxide (sold under the trade designation MT150W) | 10 |
| 7) Purified water | to 100 |

Components 1 to 4 were mixed and heated to 70° C. and the titanium dioxide dispersed therein using a high shear mixer/homogeniser (Silverson). Components 5 and 7 were mixed, heated to 70° C. and added to the remaining ingredients with stirring. The resulting mixture was homogenised to give a soft cream/lotion.

COMPARATIVE EXAMPLE E

| | |
|---|---|
| 1) Ethoxylated (2) stearyl alcohol (sold under the trade name Brij 72) | 2 |
| 2) Light liquid paraffin | 7 |
| 3) Ethoxylated (21) stearyl alcohol (sold under the trade name Brij 721) | 1 |
| 4) White soft paraffin | 7 |
| 5) 1,3-Butylene glycol | 3 |
| 6) Titanium dioxide (sold under the trade designation P25) | 10 |
| 7) Acrylic acid polymer (sold under the trade name Carbopol 430) | 0.5 |
| 8) Potassium hydroxide | to pH 7 |
| 9) Purified water | to 100 |

Components 1 to 4 were mixed and heated to 70° C. and the titanium dioxide dispersed therein using a high shear mixer/homogeniser (Silverson). Components 5, 7, 8 and 9 were mixed, heated to 70° C. and added to the remaining ingredients with stirring. The resulting mixture was homogenised to give a cream.

COMPARATIVE EXAMPLE F

| | |
|---|---|
| 1) Polyglycol ceto stearate (sold under the trade name Tefose 1500) | 10 |
| 2) Titanium dioxide (sold under the trade designation MT100T) | 10 |
| 3) Isopropyl myristate | 7.5 |
| 4) Light liquid paraffin | 2 |
| 5) Polyglycerol $C_{12}$-$C_{18}$ triglyceride (sold under the trade name Labrafil M2130 CS) | 3 |
| 7) Stearic acid | 1 |
| 8) Glycerin | 10 |

| 9) Purified water | to 100 |

Components 1, 3, 4, 5 and 6 were mixed and heated to 70° C. and the titanium dioxide dispersed therein using a high shear mixer/homogeniser (Silverson). Components 7 and 8 were mixed, heated to 70° C. and added to the remaining ingredients with stirring. The resulting mixture was homogenised to give a heavy cream.

We claim:

1. A sunscreen composition comprising a water-in-oil emulsion which comprises:
    (a) 0.5 to 30% by weight of titanium dioxide having a mean particle size of less than 100 nm;
    (b) 10 to 50% by weight of an oil phase selected from the group consisting of paraffin, mineral oil, beeswax, paraffin wax, sunflower oil, apricot kernel oil, shea butter, jojoba oil, dimethicone, cyclomethicone, cetyldimethicone and mixtures thereof;
    (c) 1 to 15% by weight of an emulsifier selected from the group consisting of (i) polyglycerol-2-sesquioleate in combination with polyethoxylated esters of hydrogenated castor oil, (ii) sorbitan sesquioleate and (iii) a silicone polyol;
    (d) at least 40% by weight of an aqueous phase.

2. A sunscreen composition as claimed in claim 1 wherein the mean primary particle size of the titanium dioxide is between 1 and 100 nm.

3. A sunscreen composition as claimed in claim 1 wherein the mean primary particle size of the titanium dioxide is between 5 and 50 nm.

4. A sunscreen composition as claimed in claim 1 wherein the titanium dioxide particles are coated with aluminum stearate.

5. A sunscreen composition as claimed in claim 1 wherein the composition comprises 2.5 to 10% of titanium dioxide.

6. A sunscreen composition as claimed in claim 1 wherein the composition contains 0.1 to 10% of a further sunscreening agent.

7. A sunscreen composition as claimed in claim 1 which contains from 0.1 to 10% of a further sunscreening agent selected from a) p-aminobenzoic acids and esters and derivatives thereof, b) methoxycinnamate esters c) benzophenones, d) dibenzoylmethanes and e) salicylate esters.

* * * * *